US008352015B2

(12) United States Patent
Bernstein et al.

(10) Patent No.: US 8,352,015 B2
(45) Date of Patent: Jan. 8, 2013

(54) LOCATION TRACKING OF A METALLIC OBJECT IN A LIVING BODY USING A RADAR DETECTOR AND GUIDING AN ULTRASOUND PROBE TO DIRECT ULTRASOUND WAVES AT THE LOCATION

(75) Inventors: Assaf Bernstein, Givaat-Nily (IL); Uriel Weinstein, Mazkeret Batia (IL); Vered Cohen Sharvit, Jerusalem (IL); Dov Oppenheim, Jerusalem (IL)

(73) Assignee: Kyma Medical Technologies, Ltd., Kfar Saba (IL)

( * ) Notice: Subject to any disclaimer, the term of this patent is extended or adjusted under 35 U.S.C. 154(b) by 1200 days.

(21) Appl. No.: 12/127,544

(22) Filed: May 27, 2008

(65) Prior Publication Data

US 2009/0299175 A1    Dec. 3, 2009

(51) Int. Cl.
*A62B 5/00* (2006.01)
(52) U.S. Cl. ........................................ 600/424; 600/454
(58) Field of Classification Search .................. 600/424, 600/454, 407
See application file for complete search history.

(56) References Cited

U.S. PATENT DOCUMENTS

| | | | |
|---|---|---|---|
| 4,825,880 A | 5/1989 | Stauffer et al. | |
| 5,807,257 A | 9/1998 | Bridges | |
| 5,829,437 A | 11/1998 | Bridges | |
| 5,967,986 A * | 10/1999 | Cimochowski et al. | 600/454 |
| 6,019,724 A | 2/2000 | Gronningsaeter et al. | |
| 6,061,589 A | 5/2000 | Bridges et al. | |
| 6,093,141 A * | 7/2000 | Mosseri et al. | 600/1 |
| 6,193,669 B1 * | 2/2001 | Degany et al. | 600/486 |
| 6,526,318 B1 | 2/2003 | Ansarinia | |
| 6,592,518 B2 | 7/2003 | Denker et al. | |
| 6,940,457 B2 | 9/2005 | Lee et al. | |
| 7,020,508 B2 | 3/2006 | Stivoric et al. | |
| 7,122,012 B2 | 10/2006 | Bouton et al. | |
| 7,280,863 B2 * | 10/2007 | Shachar | 600/424 |
| 7,493,154 B2 * | 2/2009 | Bonner et al. | 600/424 |
| 7,697,972 B2 * | 4/2010 | Verard et al. | 600/424 |

(Continued)

FOREIGN PATENT DOCUMENTS

WO    WO2009/152625    12/2009

OTHER PUBLICATIONS

Haude et al., Intracoronary Doppler- and Quantitative Coronary Angiography-Derived Predictors of Major Adverse Cardiac Events After Stent Implantation, Mar. 6, 2001, Circulation, vol. 103(9), p. 1212-1217.*

(Continued)

*Primary Examiner* — Jacqueline Cheng
(74) *Attorney, Agent, or Firm* — Mintz Levin Cohn Ferris Glovsky and Popeo, P.C.

(57) ABSTRACT

A method and apparatus are provided for determining and tracking location of a metallic object in a living body, and then directing a second modality such as ultrasound waves to the determined location. The metal detector may be a radar detector adapted to operate on a living body. The adaption may include disposing a transfer material having electromagnetic properties similar to the body between the radar detector and the living body, ECG gating the radar detector, and/or employing an optimal estimator with a model of expected stent movement in a living body. Applications include determination of extent of in-stent restenosis, performing therapeutic thrombolysis, or determining operational features of a metallic implant.

36 Claims, 7 Drawing Sheets

U.S. PATENT DOCUMENTS

| | | |
|---|---|---|
| 7,719,280 B2 | 5/2010 | Lagae et al. |
| 7,747,302 B2 | 6/2010 | Milledge et al. |
| 2002/0032386 A1 | 3/2002 | Sackner et al. |
| 2002/0045836 A1 | 4/2002 | Alkawwas |
| 2004/0077952 A1 | 4/2004 | Rafter et al. |
| 2004/0261721 A1 | 12/2004 | Steger |
| 2005/0245816 A1 | 11/2005 | Candidus et al. |
| 2007/0016050 A1 | 1/2007 | Moehring et al. |
| 2007/0135721 A1 | 6/2007 | Zdeblick |
| 2007/0191733 A1 | 8/2007 | Gianchandani et al. |
| 2008/0027313 A1 | 1/2008 | Shachar |
| 2008/0097199 A1 | 4/2008 | Mullen |
| 2008/0129511 A1 | 6/2008 | Yuen et al. |
| 2008/0167566 A1 | 7/2008 | Unver et al. |
| 2008/0200802 A1 | 8/2008 | Bahavaraju et al. |
| 2008/0294036 A1 | 11/2008 | Hoi et al. |
| 2009/0048500 A1 | 2/2009 | Corn |
| 2009/0076350 A1 | 3/2009 | Bly et al. |
| 2009/0187109 A1 | 7/2009 | Hashimshony |
| 2009/0203972 A1 | 8/2009 | Heneghan et al. |
| 2009/0227882 A1 | 9/2009 | Foo |
| 2009/0240133 A1 | 9/2009 | Friedman et al. |
| 2009/0281412 A1 | 11/2009 | Boyden et al. |
| 2010/0056907 A1 | 3/2010 | Rappaport et al. |

OTHER PUBLICATIONS

Beyer-Enke et al., Intra-arterial Doppler flowmetry in the superficial femoral artery following angioplasty., 2000, European Radiology, vol. 10, No. 4, p. 642-649.*

Ringer et al., Follow-up of Stented Carotid Arteries by Doppler Ultrasound, Sep. 2002, Neurosurgery, vol. 51, No. 3, p. 639-643.*

Kantarci et al., Follow-Up of Extracranial Vertebral Artery Stents with Doppler Sonography., Sep. 2006, American Journal of Roentgenology, vol. 187, p. 779-787.*

Ghosh, et al., Immediate Evaluation of Angioplasty and Stenting Results in Supra-Aortic Arteries by Use of a Doppler-Tipped Guidewire, Aug. 2004, American Journal of Neuroradiology, vol. 25, p. 1172-1176.*

* cited by examiner

LOCATION TRACKING OF A METALLIC OBJECT IN A LIVING BODY USING A RADAR DETECTOR AND GUIDING AN ULTRASOUND PROBE TO DIRECT ULTRASOUND WAVES AT THE LOCATION

FIELD OF THE INVENTION

This invention relates generally to an apparatus and method for determining and tracking location of a metallic object in a living body, and for guiding a second modality, for example, ultrasound, to the determined location. The invention has applicability to the general field of diagnostic imaging, and, is particularly advantageous for determining the extent of in-stent restenosis.

BACKGROUND ART

Cardiovascular disease is today considered the main cause for mortality in the Western world. Such cardiovascular diseases include atherosclerosis in which plaque builds up on the inside of arteries. Plaque is made up of fat, cholesterol, calcium and other substances found in the blood. Over time, the plaque hardens and narrows the arteries reducing the flow of oxygen-rich blood to organs and other parts of the body. This can lead to serious problems, including heart attack, stroke or even death.

Atherosclerosis can affect any artery in the body, including arteries in the heart, brain, arms, legs and pelvis. As a result, different diseases may develop based on which arteries are affected. When plaque builds up in the coronary arteries reducing or blocking blood flow to the heart, it can lead to chest pain and heart attack. This is referred to as coronary artery disease (CAD), also called heart disease, and it is currently the leading cause of death in the United States. Carotid artery disease occurs when plaque builds up in the carotid arteries that supply oxygen-rich blood to the brain. When blood flow to the brain is reduced or blocked, it can lead to a stroke. Peripheral arterial disease occurs when plaque builds up in the major arteries that supply oxygen-rich blood to the legs, arms and pelvis. When blood flow to these parts of the body is reduced or blocked, it can lead to numbness, pain and, sometimes, dangerous infections.

A common treatment for atherosclerosis comprises insertion of a stent into the narrowed blood vessel via angioplasty to prevent or counteract the localized flow constriction. Stents are typically made of metal mesh, e.g. stainless steel. After expansion by balloon angioplasty with a stent, plaque is pushed back and the artery wall stretches allowing increased blood flow. The stent prevents the stretched blood vessel from reverting to its initial size.

Unfortunately, as a result of neo-intimal tissue growth, in-stent restenosis may occur narrowing the treated blood vessel over time. In-stent restenosis is defined as greater than 50% stenosis and is estimated to occur up to 30% in bare metal stents and 7%-11% in drug eluding stents.

Existing protocols for detecting and determining extent of in-stent restenosis include catheterization, and imaging. However, catheterization is an invasive process with a high rate of complications, and existing non-invasive diagnostic protocols only provide indirect measurement. Accordingly, post stenting follow-up is significantly impaired, being neither sensitive nor specific enough, and not fully safe.

A need thus exists for a non-invasive tool for diagnosing and monitoring in-stent restenosis. More particularly, there is a need to precisely determine and track the location of a stent within a living body and then directly measure vascular flow within the stent.

More generally, a need exists for a non-invasive tool for in-vivo localization and diagnosis of metallic objects, such as artificial heart valves, orthopedic implants and screws, metallic shrapnel, and the like.

BRIEF SUMMARY OF THE INVENTION

These and other needs are met, and additional benefits and advantages achieved, according to one aspect of the present invention, by the provision of apparatus for use in diagnostic imaging. The apparatus includes a metal detector for determining location of a metallic object in a living body, an ultrasound probe, and guiding means for directing the probe at the location determined by the metal detector. The metal detector may also track the location of the metallic object in the living body. The metal detector may comprise a magnetometer, or, preferably, a radar detector. The radar detector preferably: operates in a bandwidth of several Gigahertz at a frequency in the range of 1-10 GHz, is multi-static, and employs a localization scheme based on super-resolution techniques.

The apparatus may further comprise an interface for coupling the radar detector to the living body. The interface can comprise a transfer material having electromagnetic properties similar to the body. A container may surround the transfer material, with the container situated between and in intimate contact with the radar detector and the body. In an advantageous embodiment, the antenna of the radar detector may be substantially planar, and the container rests on the substantially planar antenna with a first surface of the container adjacent the antenna and an opposite surface of the container adjacent and conforming to the body.

Various guiding means can be used to direct the ultrasound probe at the location determined by the metal detector. The guiding means may comprise a rigid attachment between the metal detector and the ultrasound probe, or a tracking system for locating the probe relative to the detector. The tracking system may preferably employ electromagnetic tracking, and at least one of the metal detector and the ultrasound probe may include a tracking element.

The guiding means may also comprise a physical framework substantially fixed in location relative to the body. The metal detector and the ultrasound probe can be mounted to this framework. Advantageously, the ultrasound probe may be mounted to the framework by a mechanical tracking device.

The guiding means may also comprise a tracking system and fiducial markers. The markers may be substantially fixed in location relative to the body and detectable by both the metal detector and the tracking system.

The guiding means may also include a component for electronic steering of an ultrasound beam of the probe to the location determined by the metal detector.

The apparatus may further include a display for presenting instructions to an operator for directing the ultrasound probe to the location determined by the metal detector. The instructions may be textual and/or graphic and may be presented on the same or a supplemental display screen as the ultrasound image. Auditory, tactile or other modes of instruction may also be employed.

In one preferred embodiment, the metal detector comprises a radar detector having an antenna in the form of an adhesive conforming patch adapted to be removably attached to the living body. The patch may include a tracking element. The patch may be designed as a single use disposable component.

In a preferred application, the metallic object comprises a stent, and the ultrasound probe measures blood velocity within the stent in order to determine extent of in-stent restenosis.

Thus, in another aspect, the present invention provides apparatus for in-vivo determination of extent of restenosis within a stent deployed in a body of a person or animal. This apparatus includes a radar detector for determining and tracking location of the deployed stent within the body, an ultrasound probe for measuring fluid flow, and guiding means for establishing a common geometric frame of reference for the radar detector and the ultrasound probe, and for guiding the probe to measure fluid flow at the location determined by the radar detector, whereby extent of in-stent restenosis can be determined from measured fluid flow.

The radar detector may be adapted to a living body by employing at least one of: a transfer material having electromagnetic properties similar to the body, ECG gating, and an optimal estimator with a model of expected stent movement in a living body.

The present invention also contemplates a method for locating a metallic object in a living body, comprising: adapting a radar detector to interface with the living body, directing a radar beam from the radar detector at the body to produce a returned radar signal, receiving the returned radar signal, and determining and tracking location of the metallic object in the living body from the returned radar signal. This method may further include directing ultrasound waves to the location determined from the returned radar signal. The ultrasound waves may be directed to the determined location for measuring fluid flow or for therapeutic purposes.

In another application, the metallic object may comprise an artificial heart valve, and the method may further include the step of determining operational feature(s) of the valve from the returned radar signal.

The radar detector may be adapted to the living body by disposing a transfer material having electromagnetic properties similar to the body between the radar detector and the living body, and/or ECG gating the radar detector, and/or employing an optimal estimator with a model of expected stent movement in a living body.

The method may also include registering a three-dimensional arterial map of the living body, reconstructed from angiography images, to the determined location of the metallic object, and guiding a modality other than radar to the determined location of the metallic object and/or a different correlated location on the arterial map.

In a further aspect, the current invention provides a method for determining fluid flow within a metallic object in a living body. This method includes metallic object localization by determining and tracking location of the metallic object in the body with a metal detector; guiding an ultrasound probe to the location determined by the metal detector; and measuring fluid flow at the location with the ultrasound probe. The guiding may include registering the ultrasound probe and the metal detector to a common geometric frame of reference, and such registration may be performed automatically.

The metallic object localization may be performed continuously on-line during fluid flow measurement, or periodically or at a single instance. Fluid flow measuring may be performed at several locations near the metallic object and/or performed at different times and measurement results compared.

In still another aspect, the present invention provides a method for determining extent of restenosis within a stent deployed in a living body comprising the steps of: determining and tracking location of the deployed stent in the body with a radar detector; measuring fluid flow with an ultrasound probe at the location determined by the radar detector; and determining extent of restenosis within the deployed stent from measured fluid flow.

The present invention affords numerous benefits and advantages. It provides a non-invasive, non-ionizing tool for diagnosing and monitoring in-stent restenosis by combing radar and ultrasound Doppler modalities. It enables precise determination and tracking of location of a metallic stent or other metallic object in a living body, and facilitates direct vascular flow measurement within deployed stents. Post stenting follow-up is thus significantly improved.

The present invention enables an ultrasound Doppler in-stent flow measurement enhanced by a radar or other metallic object locator. The radar detector may be especially adapted for in-vivo application. Various guidance approaches and tracking systems may be employed to guide the ultrasound probe based on the metallic object localization. Guidance instructions can be provided to the operator visually, audibly or otherwise, allowing simple, efficient, and accurate real-time operation. The metallic object locator and probe guidance components can be readily added to existing ultrasound machines or systems.

In addition to diagnostic and imaging applications, the present invention may be used for therapeutic purposes or to monitor implanted devices such as artificial heart valves. When combined with a 3 dimensional arterial map, other locations can be readily targeted.

The present invention may also be advantageously applied to in-vivo localization and diagnosis of metallic shrapnel and of orthopedic objects such as implants and screws, and to assessing the danger posed by metallic objects for patients expected to undergo MRI scanning.

BRIEF DESCRIPTION OF THE DRAWING FIGURES

Preferred embodiments of the present invention will now be described in relation to the accompanying drawing figures, in which:

FIG. 2A is a blow-up of the combined instrument of FIG. 2;

DETAILED DESCRIPTION

The present invention is generally directed to a method and apparatus for determining location of a metallic object in a living body, and directing a second modality at the determined location or a related location. Although amenable to various applications, specific embodiments are described herein, by way of example and not limitation, in order to illustrate the principles and features of the invention. In the various drawing figures, common elements are designated by common reference numbers.

Figure 1:
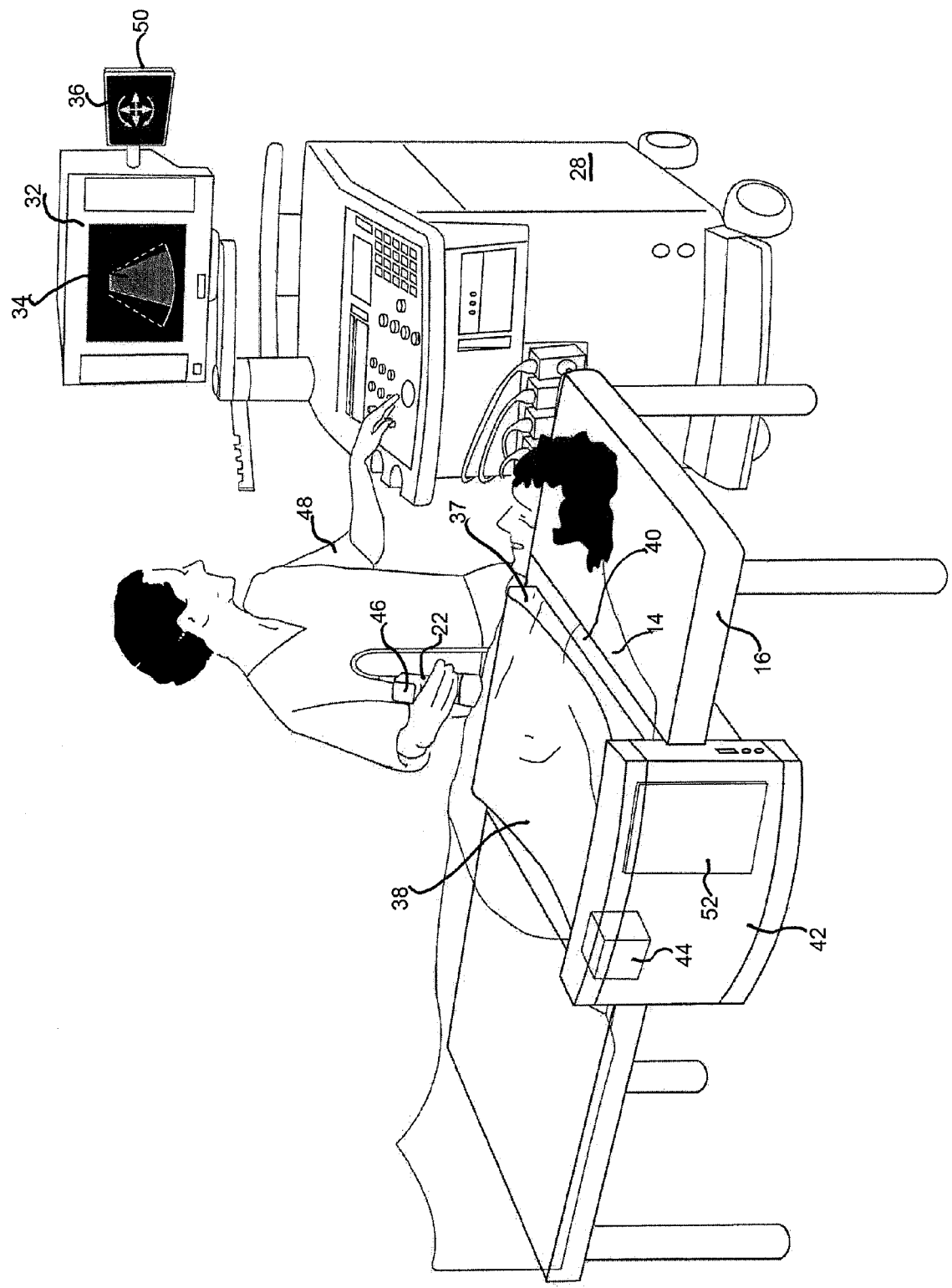
FIG. 1 illustrates the combined use of a radar detector with an ultrasound probe and a tracking system, in which an antenna of the radar detector is substantially planar and a flexible container filled with compatible transfer material is employed to adapt the radar detector to a living body.

FIG. 1 shows a first approach for precisely identifying and tracking location of a stent or other metallic object in a patient with a radar detector, and then directing ultrasound waves to the determined location. In this embodiment, the patient (14), shown as transparent, reclines on a mattress (16) or other suitable supporting surface. Embedded in, or otherwise associated with mattress (16) is a substantially planar radar antenna (40). Interposed between the radar antenna and the patient's body is a container or cushion (37) having an upper surface (38) that conforms to the shape and contour of the portion of the patient's body in contact with the cushion. Cushion (37) is preferably filled with a transfer material having electromagnetic properties similar to those of the body. An exemplary transfer material might be a solution of about 85% ethylene glycol and about 15% water. Other materials, e.g. gel or liquid, which mimic the electromagnetic properties of the body can be used as the transfer material. Similarly, cushion or container (37) may be made of any suitable material that allows for intimate contact with the antenna and intimate conforming contact with the patient's body.

As more fully described hereinafter, antenna (40) is preferably a multi-static, multi-element antenna constructed as a flat panel to fit beneath the patient's back. The multi-element antenna can be a printed or patch antenna. The radar detector preferably operates in a bandwidth of several Gigahertz at a frequency in the range of 1-10 GHz. The transfer material in container (37) serves as an interface between the radar detector and the living body that reduces radar reflection caused by a skin-air interface, and thus comprises an adaption of the radar detector to the living body.

Continuing with the description of FIG. 1, a console (42) may be mounted along one side of support surface (16). Console (42) includes a tracking transmitter (44) and a central controller (52) (described hereinafter with reference to FIG. 6). Tracking transmitter (44) interacts with a tracking element, sensor or transducer 46 associated with ultrasound probe (22) and optionally, with additional tracking elements associated with radar antenna (40) or transfer material container (37). Transmitter (44) and the tracking elements form part of a tracking system employed to register the ultrasound probe to a common coordinate system with the radar detector. Although preferably electromagnetic, the tracking may be optical, mechanical or employ another suitable modality. One suitable electromagnetic tracking system is sold under the name FASTRAK by the Polhemus Company of Colchester, Vt., USA. A suitable optical tracking system is the Micron Tracker available from Claron Technology Inc. of Toronto, Ontario Canada. A useful mechanical tracking system is the MicroScribe® G2 desktop digitizing system available from Immersion Corporation of San Jose, Calif., USA. Other available tracking systems may, of course, also be used.

As more fully described hereinafter, the radar detector, operating in conjunction with the tracking system, provides instructions (36) to an operator (48) for directing the ultrasound probe (22) at the precise location of a stent or other metallic object in the living body, as determined by the adapted radar detector. Instructions (36) may be presented on a supplemental display (50) located adjacent the display (32) so that both instructions (36) and ultrasound image (34) of the stent and its vicinity, are within the field of view of operator (48). Display (50) may, of course, be positioned in different locations or could be combined with display (32) of the conventional ultrasound machine. Instructions (36) may be textual and/or graphic or otherwise visually presented. Such instructions can also be presented in auditory, tactile or other fashion to the operator.

Figure 2:
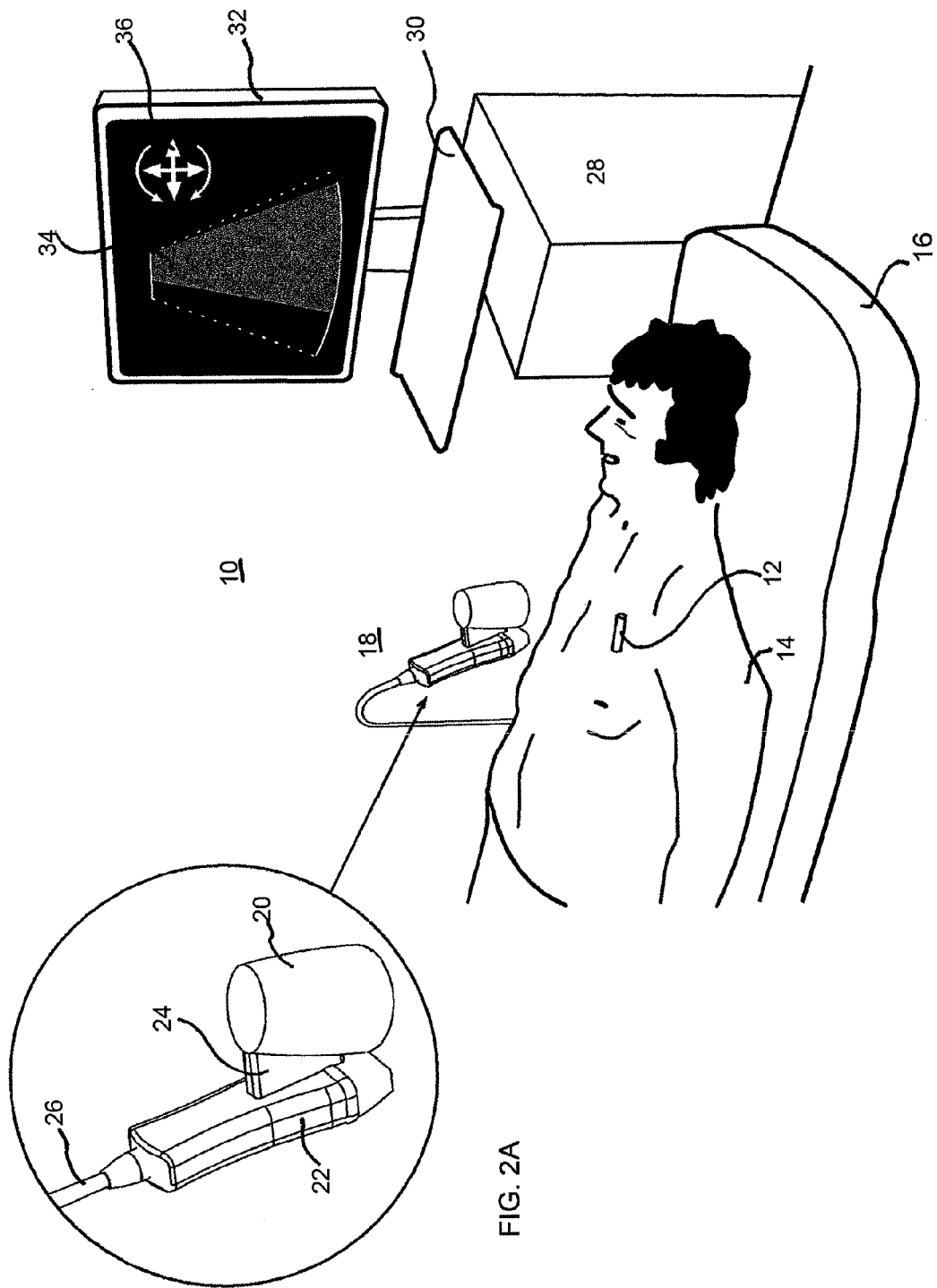
FIG. 2 depicts apparatus for determining location of a stent in a living body which employs a rigidly connected ultrasound probe and metal detector.

FIG. 2 depicts an alternate embodiment of a system (10) for locating a metal stent (12) in a living person (14) and directing an ultrasound probe (22) to the determined location. As illustrated, a patient having a previously implanted stent (12) reclines on a mattress (16), bed or other suitable support surface. A combined instrument (18) determines in-vivo the location of stent (12) and directs ultrasound waves to the determined location.

As more clearly seen in the magnified view of FIG. 2A, combined instrument (18) includes a standard ultrasound probe (22) rigidly connected by any suitable physical arrangement (24) to a metal detector (20). Metal detector (20) may comprise a magnetometer, for example, of the pulse-induction type, or other metal detector. The rigid connection between ultrasound probe (22) and metal detector (20) ensures registration, i.e. both operate in the same coordinate system. Thus, the rigid connection serves to guide and direct the ultrasound probe at a location of the stent or other metallic object in the living body determined by the metal detector.

Electronic & RF cabling (26) connects ultrasound probe (22) to an ultrasound machine (28). Optionally, metal detector (20) can also be electrically connected by cable (26) to its operational control unit.

Ultrasound machine (28) typically includes an operator control and input device (30) and a display (32) for presenting an ultrasound image (24).

In operation, metal detector (20) is used to detect, determine location and, preferably, track location of stent (12) within patient (14). The metal detector provides instructions (36), overlaid on the same display screen as ultrasound image (34) or presented on a supplemental display monitor, to guide an operator in directing ultrasound probe (22) to the stent location determined by the metal detector. Rigid connection (24) provides automatic registration between the ultrasound probe (22) and metal detector (20), thereby ensuring operation in a common coordinate system.

Figure 3:
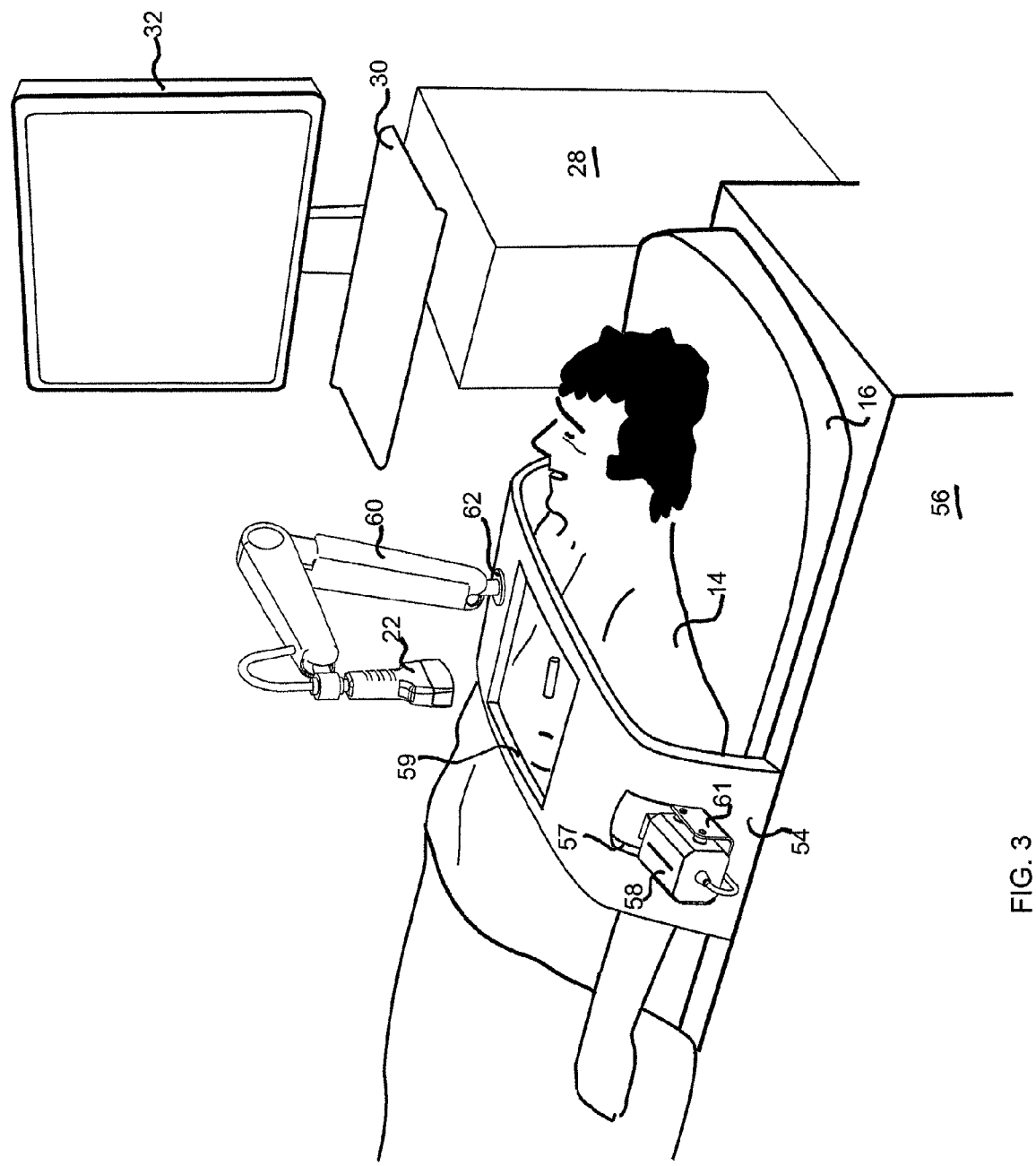
FIG. 3 depicts an embodiment in which a radar detector and ultrasound probe are registered by mounting to a physical framework substantially fixed in relation to the living body.

In FIG. 3, a physical framework (54) is associated with a support structure (56) on which mattress (16) and patient (14) reside. Patient (14) is preferably located in a fixed position relative to framework (54).

Framework (54) preferably includes apertures (57) and (59) therethrough. Framework (54) supports a radar detector (58), or other metal detector, adjacent aperture (57), and ultrasound probe (22) above aperture (59). Radar detector (58) is fixed in position relative to framework (54) by a bracket (61), or other suitable mounting hardware. Ultrasound probe (22) is preferably mounted to framework (54) by a base (62) of a mechanical supporting and tracking unit (60). The mechanical supporting and tracking unit can include articulated arms facilitating three-dimensional positioning of probe (22), and appropriate sensors for tracking the position of the probe relative to base (62) and framework (54). For example, a MicroScribe G2 desktop digitizing system available from Immersion Corporation can be used as the mechanical supporting and tracking unit. The mechanical supporting and tracking unit (60) may also be a robotic active element that receives direct movement commands from the metal detector and automatically directs the ultrasound probe to the target, thereby compensating for patient movement, breathing and heart beat. Framework (54) with its rigid attachment of radar detector (58) and base (62) of the mechanical supporting and tracking device affords registration to a common coordinate system of the radar detector and ultrasound probe. Apertures (57) and (59) in framework (54) afford unimpeded radar and ultrasound wave transmission, respectively.

Figure 4A:
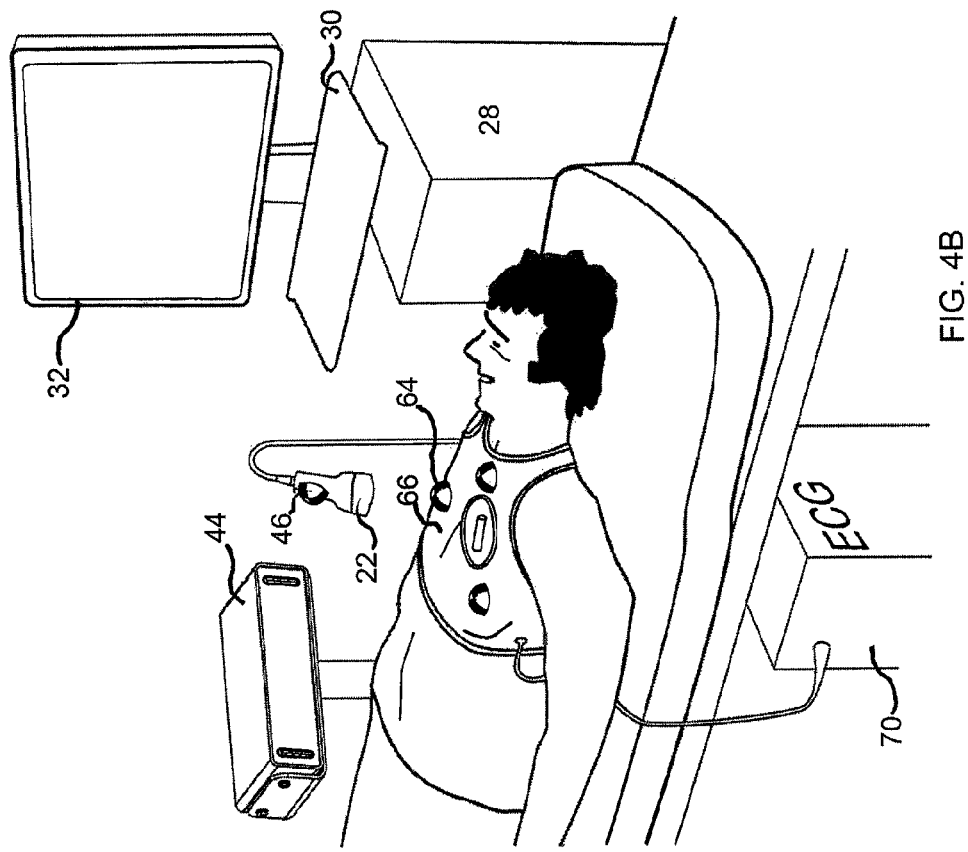
FIG. 4A depicts a first stage in which a radar detector determines location of a stent using fiducial markers worn by a patient.

In FIG. 4A, patient (14) wears a vest (66), or a partially-rigid apparel, designed to remain in the same position on the body whenever worn, having a set of fiducial markers (64) for registration of a radar detector (58). The fiducial markers (64) are in a predetermined position relative to patient (14), and may, alternatively, be applied directly to the patient's body. The markers may take various forms provided that they are detectable both by a radar (or other metal) detector and by a tracking system.

In the first stage, illustrated in FIG. 4A, radar detector (58) determines and tracks location of stent (12) within patient (14) relative to fiducial markers (64).

Figure 4B:
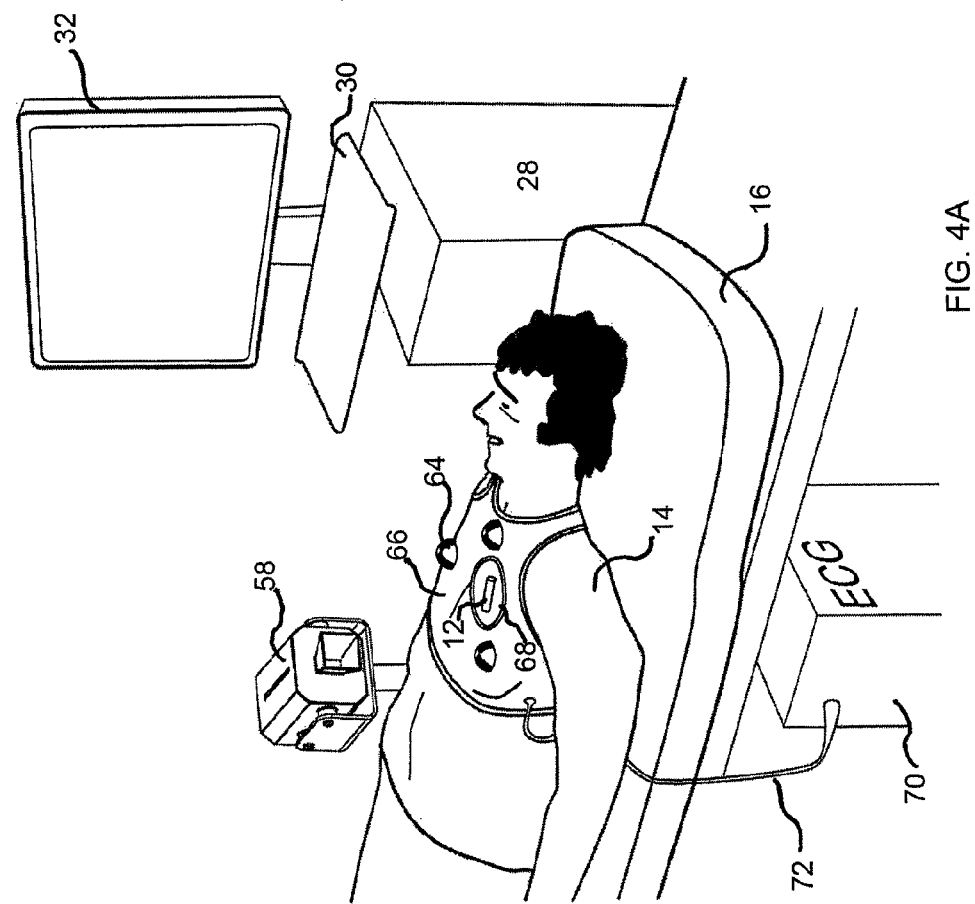
FIG. 4B shows a second stage in which an ultrasound probe can be guided to the determined location of the stent using the same fiducial markers and a tracking system.

In a second stage, illustrated in FIG. 4B, a tracking system (44) determines the location of ultrasound probe (22) relative to fiducial markers (64). To facilitate such tracking, an additional fiducial marker (46) or other tracking element is associated with ultrasound probe (22).

As also illustrated in FIGS. 4A and 4B, vest (66) is preferably provided with an aperture (68) overlying the general area in which the stent is located. Aperture (12) minimizes interference of vest (66) with ultrasound probe (22). Optionally, radar detector (58) may be gated by an ECG signal from electrocardiogram machine (70), as more fully described hereinafter.

Figure 5:
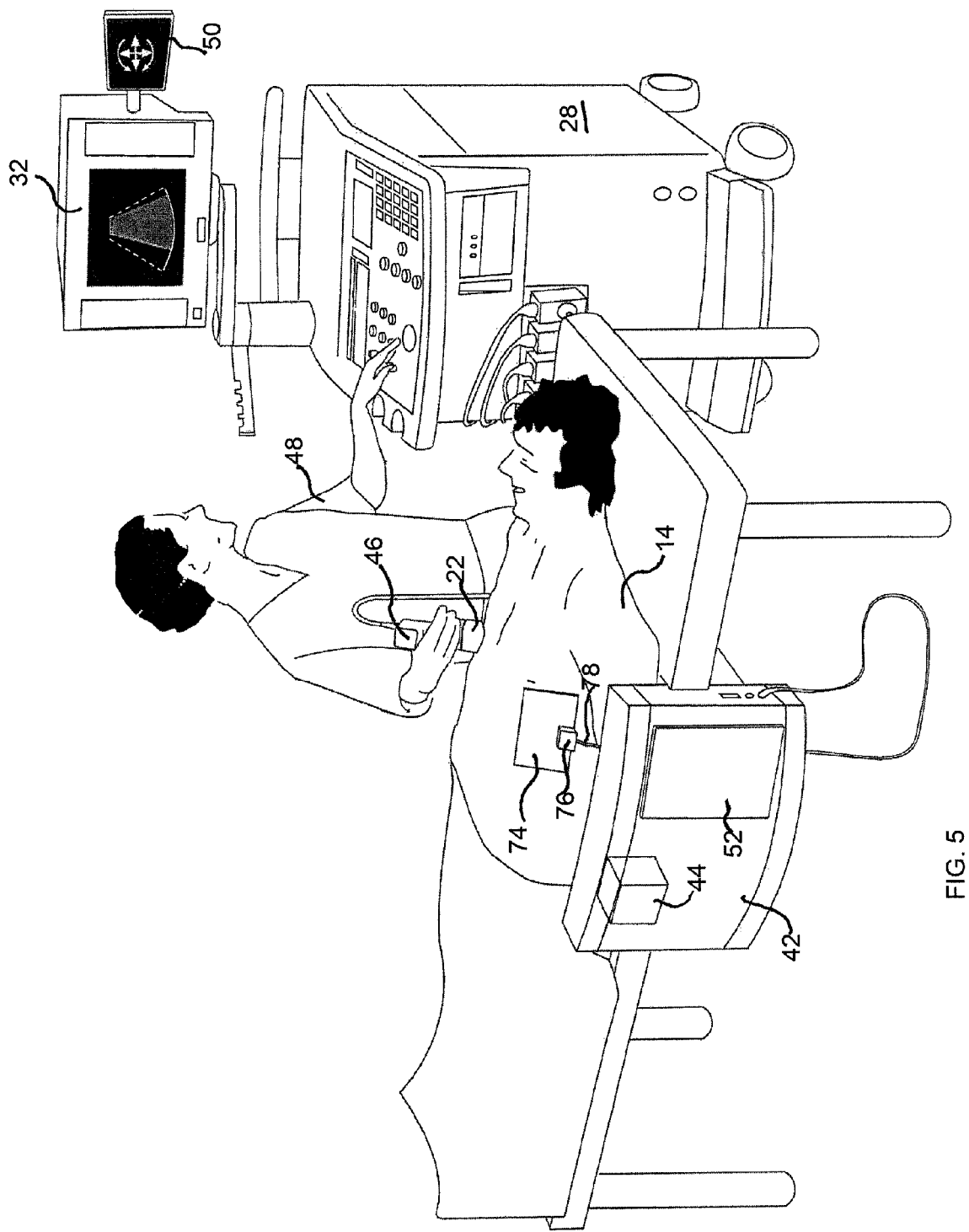
FIG. 5 depicts an embodiment employing an antenna patch having a tracking element.

The embodiment of FIG. 5 is similar to that of FIG. 1, but instead of a substantially planar radar antenna placed under the patient, the radar antenna may comprise a conforming patch (74) adapted to be removably attached to patient (14), e.g. near the heart. In known fashion, patch (74) may be provided with a skin compatible adhesive coating for temporary connection to the body. Patch (74) can be provided with a tracking element or transducer (76) for tracking its location, and may be provided with an electronic cable (78) for connecting the patch to the rest of the radar detector. The patch may contain a printed radar antenna. One advantage of this embodiment is the direct coupling of the radar antenna to the patient's body; another advantage is that the patch may be disposable after a single use.

Figure 6:
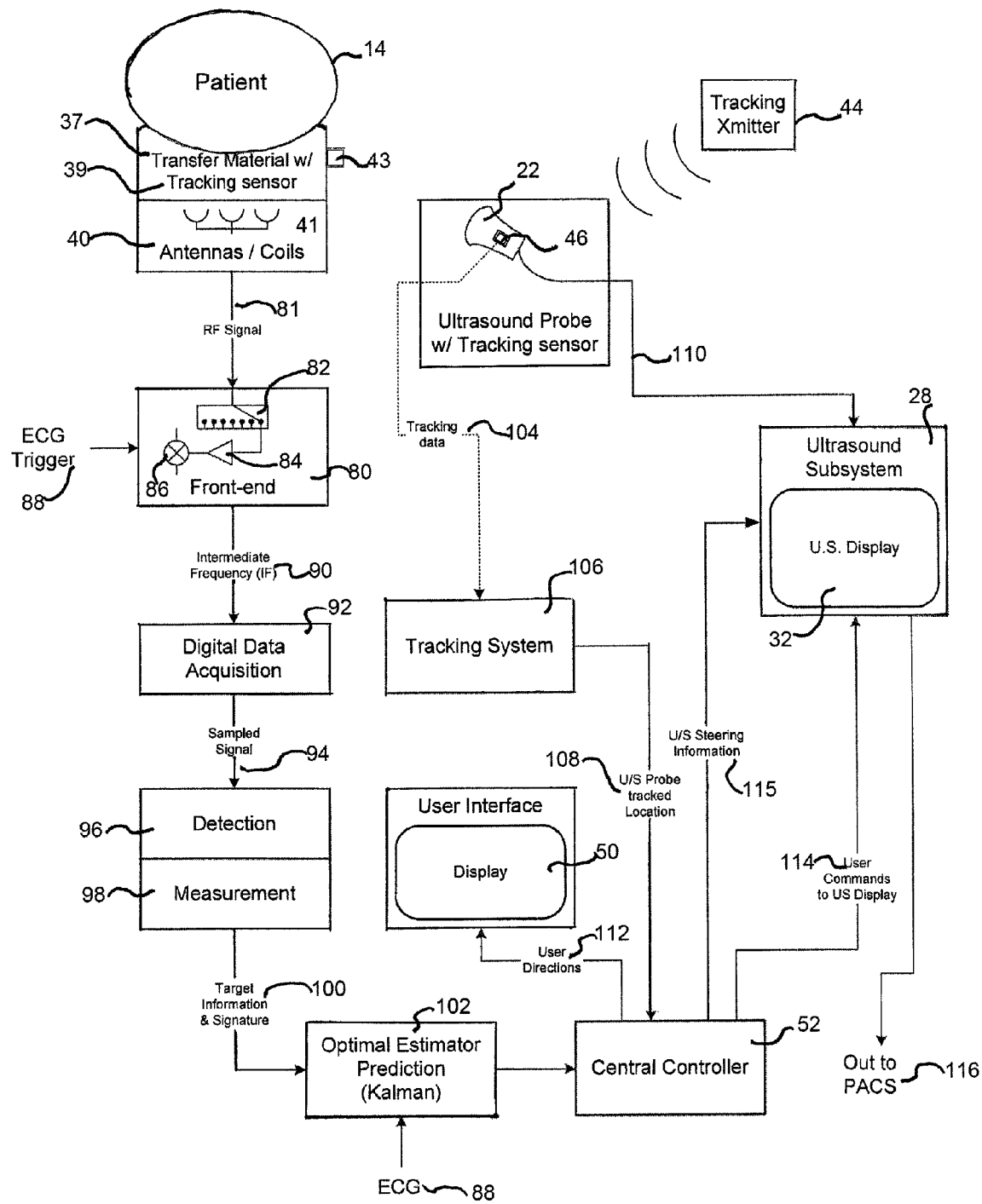
FIG. 6 is a block diagram of one preferred embodiment of the apparatus of the present invention.

FIG. 6 depicts one preferred configuration, in block diagram form, of the apparatus of the present invention. As earlier described, patient (14) can be located on a cushion (37) containing transfer material (39), atop a multi-element substantially planar antenna (40). A tracking element (43) may be associated with cushion (38) and/or antenna (40) for tracking purposes. The multi-static, multi-element antenna can be a printed or patch antenna constructed and operated in know fashion. Additionally, the antenna may be customized and adapted to a living body by creating an electromagnetic field pattern or aperture that can be focused or pointed at a precise location within human tissue while immersed in or enfolded by a transfer material.

In order to reduce reflection at the air-skin interface, the antenna is surrounded by a transfer material with electromagnetic properties similar to that of the body. The high dielectric constant of the transfer material also allows the antenna to be smaller because the wavelength is significantly smaller in such a substance as in the body. The transfer material is suspended in a cushion or other container touching the antenna and extending above it until the cushion snuggly touches the patient's body in a conforming way, allowing direct line-of-sight from the entire antenna to the metallic target, without passing through air. In place of antenna elements, multiple coils may be used for magnetic determination of location of the metallic object.

Outputs of the antenna elements (or magnetic coils) (41) are acquired into the system. In order to avoid many radar receivers, the different antenna elements can either be switched consecutively into one or more receivers or modulated in orthogonal modulations and summed into one or more RF signal(s) (81), in known fashion. This modulation can be achieved by adding a printed layer to the antenna with modulating diodes on it, or by other known techniques.

RF signal(s) (81) is fed into front-end module (80) of the radar detector. The RF chain within front-end module (80) includes switching/modulating matrix (82), amplifier (84), mixer (86) and other conventional components. In addition to the switching/modulation function, in front-end module (80), the RF signal(s) from the antenna elements are amplified, using low-noise amplifiers, band-pass filtered, and down-converted into coherent IF signals (90). The IF signals may retain the inter-element amplitude and phase information, and can be later used to detect, locate and track the metallic object in the living body in different locations in space.

The IF signals are sampled in a digital data acquisition module (92), where they are converted into digital information streams. If the antenna channels were modulated, they can be de-modulated using known digital signal processing techniques.

Next, all of the antenna channels contained within the sampled signal (94) are fed into the detection module (96) where they are optionally integrated coherently with different time-gating and different phase differences corresponding to the different locations in the detection space. In measurement module (98), super-resolution techniques are employed for interpolating a more accurate position for the detected target. Super-resolution techniques are well known in the radar field. Alternatively, non-coherent processing methods may be used for detection and measurement, using difference of time of arrival or amplitude ratios for determining the target location.

Target information and radar signature or other characterizing information (100) from the detection and measurement modules is then passed onto an optimal estimator (102) for estimating the target location, using a modified Kalman filter or equivalent. The characterizing information and/or radar signature may relate to orientation of the metallic object and other optional information such as Doppler velocity, other spectral and temporal characteristics and amplitude information. The same estimator is also used for predicting location of the target at certain points in time, allowing for proper control and man-machine interface. As an adaption of the radar detector to a living body, the optimal estimator can employ a model of expected stent movement in a living body. Such movement is periodic, of known amplitudes, velocities and acceleration as expected from the movement of the heart wall, according to known measurements of these values. An optimal estimator with a Kalman filter is a known measurement technique.

The estimated target position from optimal estimator (102) is then fed into a central controller (52) where it is compared to the tracked ultrasound probe location to provide directional guidance to the operator.

In the configuration shown in FIG. 6, a tracking transmitter (44) is installed close to the patient, preferably in a position least affected by metallic parts of the bed. A tracking sensor or receiver (46) is attached to standard ultrasound probe (22). Optionally, the tracking sensor can be removed when the ultrasound unit is used for other procedures. Ultrasound probe (22) is connected by cable (110) to ultrasound machine (28) in the usual manner and the ultrasound machine is used as it is normally used.

Tracking data (104) from ultrasound sensor (46) is fed into standard tracking system electronics module (106). Ultrasound probe tracked location (108) passes from module (106) to central controller (52) where it is preferably filtered according to an expected probe movement profile. Movement profile refers to velocities and accelerations expected to result from normal movement of a probe. The central controller then estimates a "region of imaging" location from the filtered probe tracked location signal and compares it with the estimated target location provided by the radar detector. A difference in location between the "region of imaging" and the predicted target location from the radar detector is used to calculate user commands or instructions (114) needed for the user to adjust the probe so as to see the target. These commands are passed to the user interface display (50) as user directions (112) or to the ultrasound display (32) as user commands (114). The central controller can also provide ultrasound steering information (115) to the ultrasound machine (28) to steer the ultrasound beam to the targeted location, as disclosed, for example, in U.S. Pat. No. 6,730,033 (which patent is hereby incorporated by reference herein).

Optionally, an ECG trigger (88) can be used to gate front-end module (80) of the radar detector to reduce the RF duty cycle by transmitting the RF signal only at certain phases of the heartbeat. ECG gating can also be used for an improved model of target motion in the optimal estimator (102). Similarly, optionally, an additional tracking sensor (not shown) can be attached to the patient to measure breathing motion and then used for improved tracking. In conventional fashion, outputs of the ultrasound machine can be provided to a PACS system (116) for medical archiving.

Figure 7:
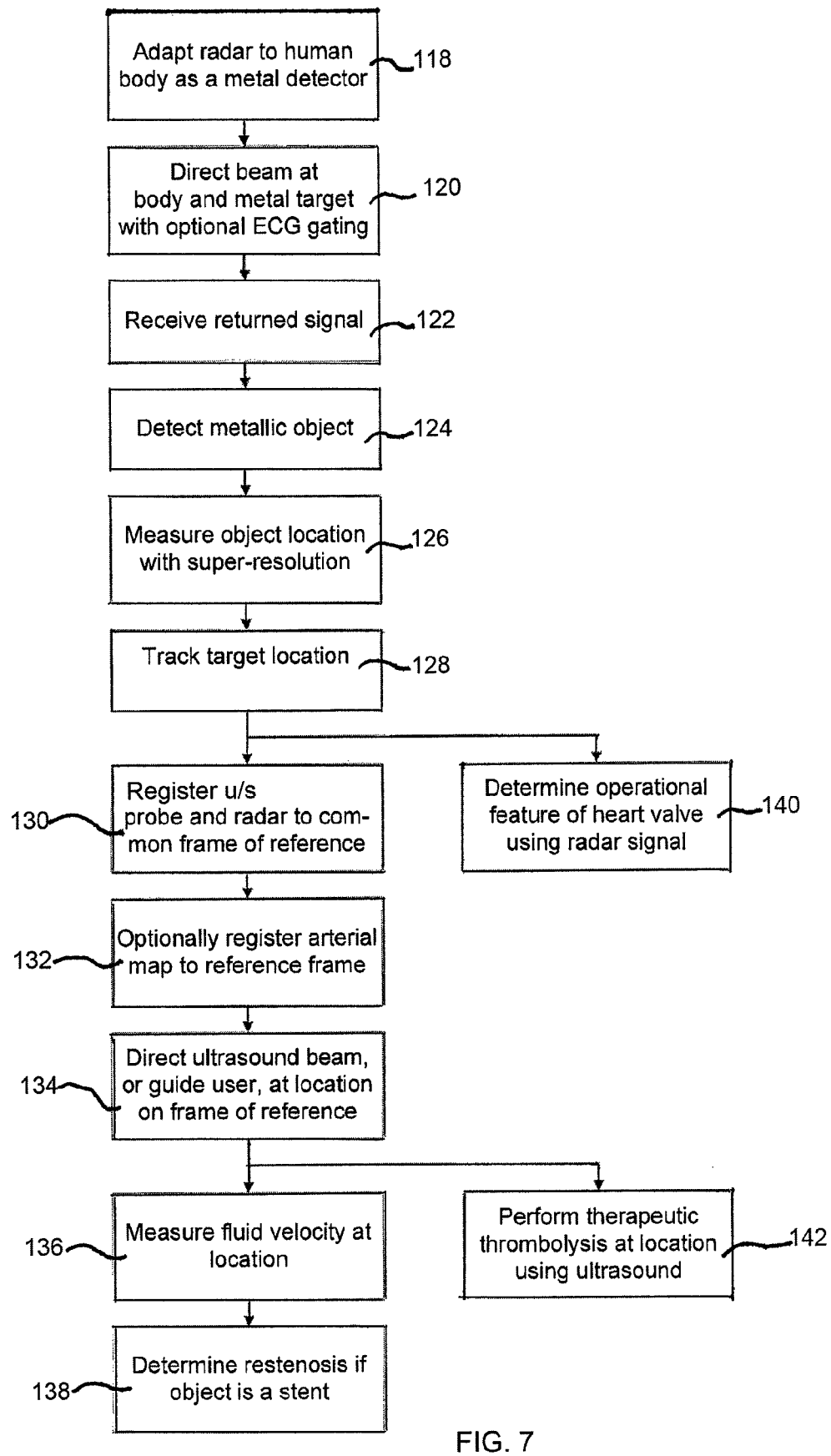
FIG. 7 provides a flow chart of methods that can advantageously be implemented by the present invention.

FIG. 7 presents a flow chart of methods that can be successfully implemented with the present invention. In an initial step (118), a radar detector is preferably adapted to serve as a detector and locator of a metallic object in a living body. Such adaption may include disposing a transfer material having electromagnetic properties similar to the body between the radar detector and the living body, ECG gating the radar detector, and/or employing an optimal estimator with a model of stent movement in a living body.

Next, the radar beam is directed at the living body and metal target, with optional ECG gating (step 120). A returned radar signal is then received (step 122), and processed as earlier described to detect the metallic object in the living body (step 124). The metallic object's location is then measured, preferably using super-resolution techniques (step 126), and its location tracked (step 128).

The ultrasound probe and radar detector (or other metallic object detector) are registered to a common frame of reference (step 130), by a tracking system, or otherwise. Optionally, a 3-dimensional map of the patient's arteries (arterial map) constructed from angiograms or cardiac CT data such as provided by Paieon Inc. of New York, N.Y., USA and including the metallic object in the map, can also be registered to this frame of reference (step 132). The ultrasound beam is then directed by user guidance provided by the central controller, for example, on a suitable display, or otherwise, to the location of the metallic object as determined by the radar detector or to another correlated location on the arterial map (step 134).

The directed ultrasound beam can be used to measure Doppler velocity of the fluid at the determined location (step 136), in known fashion. If the metallic object is a deployed stent, extent of in-stent restenosis can be determined from measured fluid velocity (step 138), via a look-up table or in other known fashion. Such techniques are disclosed, for example, in "Duplex Ultrasound Velocity Criteria For The Stented Carotid Artery" by Brajesh K Lai et al, on the Vascular Web site provided by the Society for Vascular Surgery at: http://www.vascularweb.org/Annual_Meeting/Abstracts/2007/lal_duplex_ultrasound_velocity.html and in the Inaugural issue of the newsletter of the Vascular Diagnostic Laboratory published by the Heart and Vascular Institute of Morristown, N.J., at: http://www.franklynideas.com/hvi_s-ite/hvi2_newsevents newsletter.html (which publications are hereby incorporated by reference herein).

Alternatively, the directed ultrasound beam may be employed to perform therapeutic thrombolysis at the determined location (step 142). Optionally the method used can be HIFU (high intensity focused ultrasound).

If the metallic object is an artificial heart valve, operational feature(s) of the artificial heart valve can be determined from the radar signal, signature and characterizing information provided by the radar detector (step 140). Such characterizing information may be the radar Doppler velocity of a valve along time, characterizing operational features such as the speed and the travel distance at which a valve operates.

In other applications, a modality other than radar or ultrasound may be directed to the determined location of the metallic object, or to a different location on the arterial map.

The metallic object localization of the present invention may be performed continuously on-line during fluid flow measurement (which is especially appropriate to the configuration depicted in FIGS. 4A and 4B), or periodically, or at a single instance. Similarly, the measurement of fluid flow may be performed at several locations near the metallic object to observe blood flow before and after obstructions. Fluid flow measurement can also be performed at different times and measurement results compared; for instance, one measurement immediately after stent placement as a baseline for comparison to measurements at subsequent times.

From the foregoing description, it will be evident that the present invention provides a unique, non-invasive tool for precisely determining and tracking location of a metallic object, such as a stent, within a living body. Guidance can then be provided to direct ultrasound waves, or another modality, to the determined location of the metallic object, or a correlated location on a registered arterial map, for diagnostic, therapeutic or other purposes. As such, the present invention provides a significant advance in medical diagnosis, imaging and treatment. Although various embodiments have been described and depicted herein, it will be apparent to those skilled in the art that various modifications, substitutions and additions can be made without departing from the scope of the present invention, as defined by the appended claims.

The invention claimed is:

1. An apparatus for use in diagnostic imaging, comprising:
   a radar detector comprising an antenna configured as a conforming patch for removable attachment to a living body, wherein the radar detector determines and tracks the location of a metallic object in a living body;
   an ultrasound probe; and
   guiding means for directing said probe at the location determined by the metal detector.

2. The apparatus of claim 1, wherein the radar detector operates in a bandwidth of several Gigahertz at a frequency in a range of 1-10 GHz.

3. The apparatus of claim 1, wherein the radar detector is multi-static.

4. The apparatus of claim 1, wherein the radar detector employs a localization scheme based on super-resolution techniques.

5. The apparatus of claim 1, further comprising an interface for coupling the radar detector to the living body.

6. The apparatus of claim 5, wherein the interface comprises a transfer material having electromagnetic properties similar to the body.

7. The apparatus of claim 6, wherein the interface further comprises a container surrounding the transfer material, and the container is situated between and in intimate contact with said radar detector and the body.

8. The apparatus of claim 7, wherein the antenna of the radar detector is substantially planar, the container rests on said substantially planar antenna, a first surface of the container is adjacent the antenna, and an opposite surface of the container is adjacent and conforms to the body.

9. The apparatus of claim 1, wherein the guiding means comprises a tracking system for locating the probe relative to the detector.

10. The apparatus of claim 9, wherein at least one of the radar detector and the ultrasound probe includes a tracking element.

11. The apparatus of claim 9, wherein the tracking system employs electromagnetic tracking.

12. The apparatus of claim 1, wherein the probe measures Doppler velocity of fluid.

13. The apparatus of claim 1, wherein the radar detector also determines orientation of the metallic object in the body.

14. The apparatus of claim 1, wherein the radar detector also measures a radar signature of the metallic object.

15. The apparatus of claim 1, wherein the metallic object comprises a stent, and the probe measures blood velocity within the stent.

16. The apparatus of claim 1, further comprising a display presenting instructions for directing the ultrasound probe at the location determined by the metal detector.

17. The apparatus of claim 1, wherein the patch includes a tracking element.

18. The apparatus of claim 1, wherein the radar detector is ECG gated.

19. An apparatus for in-vivo determination of extent of restenosis within a stent deployed in a body of a person or animal, comprising:
 a radar detector comprising an antenna configured as a conforming patch for removable attachment to a living body, wherein the radar detector determines and tracks the location of the deployed stent within the body;
 an ultrasound probe for measuring fluid flow; and
 guiding means for establishing a common geometric frame of reference for the radar detector and the ultrasonic probe, and for guiding the probe to measure fluid flow at the location determined by the radar detector, whereby extent of in-stent restenosis can be determined from measured fluid flow.

20. The apparatus of claim 19, wherein the radar detector includes at least one of:
 a transfer material having electromagnetic properties similar to the body;
 ECG gating; and
 an optimal estimator with a model of expected stent movement in a living body.

21. A method for locating a metallic object in a living body, comprising:
 adapting a radar detector to interface with a living body, the radar detector comprising an antenna configured as a conforming patch for removable attachment to the living body;
 directing a radar beam from the radar detector at the body to produce a returned radar signal;
 receiving the returned radar signal; and
 determining and tracking location of the metallic object in the living body from the returned radar signal.

22. The method of claim 21, further comprising: directing ultrasound waves to the location determined from the returned radar signal.

23. The method of claim 22, further comprising: measuring fluid flow at the determined location with the ultrasound waves.

24. The method of claim 23, wherein the metallic object comprises a stent; and further comprising: determining extent of in-stent restenosis from measured fluid flow.

25. The method of claim 21, wherein said adapting comprises at least one of: disposing a transfer material having electromagnetic properties similar to the body between the radar detector and the living body, ECG gating the radar detector, and employing an optimal estimator with a model of expected stem movement within a living body.

26. The method of claim 21, further comprising guiding a modality other than radar to the determined location of the metallic object.

27. The method of claim 21, further comprising registering a three dimensional arterial map of said living body to the determined location of the metallic object.

28. The method of claim 27, further comprising guiding a modality other than radar to a different correlated location on the arterial map.

29. A method for determining fluid flow within a metallic object in a living body, comprising:
 adapting a radar detector to interface with a living body, the radar detector comprises an antenna configured as a conforming patch for removable attachment to the living body;
 metallic object localization by determining and tracking the location of the metallic object in the body with the radar detector;
 guiding an ultrasound probe to the location determined by the radar detector; and
 measuring fluid flow at the location with the ultrasound probe.

30. The method of claim 29, wherein said guiding includes registering the ultrasound probe and the radar detector to a common geometric frame of reference.

31. The method of claim 30, wherein said registering is performed automatically.

32. The method of claim 29, wherein the metallic object localization is performed continuously on-line during fluid flow measurement.

33. The method of claim 29, wherein the metallic object localization is performed periodically or at a single instance.

34. The method of claim 29, wherein said measuring is performed at several locations near the metallic object.

35. The method of claim 29, wherein said measuring is performed at different times and measurement results compared.

36. A method for determining extent of restenosis within a stent deployed in a living body, comprising:

adapting a radar detector to interface with a living body, the radar detector comprises an antenna configured as a conforming patch for removable attachment to a living body;

determining and tracking the location of the deployed stent in the body with the radar detector;

measuring fluid flow with an ultrasound probe at the location determined by the radar detector; and determining extent of restenosis within the deployed stent from measured fluid flow.

* * * * *